US007765881B2

(12) United States Patent  (10) Patent No.: US 7,765,881 B2
Miller et al.  (45) Date of Patent: Aug. 3, 2010

(54) PROGRAMMABLE, DIGITAL VACUUM-OPERATED LIQUID SAMPLER

(75) Inventors: John Kevin Miller, Clive, IA (US);
Tony Ray Sage, Ankeny, IA (US);
Robert M. Gilliom, Wooster, AR (US)

(73) Assignee: Electric Pump, Inc., Des Moines, IA (US)

( * ) Notice: Subject to any disclaimer, the term of this patent is extended or adjusted under 35 U.S.C. 154(b) by 503 days.

(21) Appl. No.: 11/975,446

(22) Filed: Oct. 19, 2007

(65) Prior Publication Data

US 2009/0100902 A1  Apr. 23, 2009

Related U.S. Application Data

(60) Provisional application No. 60/853,510, filed on Oct. 20, 2006.

(51) Int. Cl.
*G01N 1/00* (2006.01)
(52) U.S. Cl. .................................... 73/863.02
(58) Field of Classification Search ........................ None
See application file for complete search history.

(56) References Cited

U.S. PATENT DOCUMENTS 3,587,670 A * 6/1971 Brailsford ................ 73/864.35
3,795,347 A * 3/1974 Singer ..................... 73/864.35
3,924,471 A * 12/1975 Singer ..................... 73/864.35
4,022,059 A * 5/1977 Schontzler et al. ............ 73/198
4,077,263 A * 3/1978 Brailsford ................ 73/864.35

* cited by examiner

*Primary Examiner*—Robert R Raevis
(74) *Attorney, Agent, or Firm*—Stephen D. Carver

(57) ABSTRACT

A programmable liquid sampler for obtaining and digitally analyzing multiple, sequential samples in real time from an external source of liquid to be analyzed comprises an adaptive feedback algorithm for correcting sample weight measurements occasioned by vacuum delays. A sampling assembly receives and at least temporarily stores a sample drawn by suction through an air port that can also pressurize the chamber. A load cell determines sample mass through a logic controller that implements adaptive feedback by recognizing a desired target sample size, requesting an initial sample, and measuring the initial sample size. A variable scaling factor is derived by comparing the target sample size to said measured sample size and the subsequent requesting size is scaled. Samples can be stored in multiple compartments of a radial table that is indexed by the computer software for proper sample control.

18 Claims, 12 Drawing Sheets

PROGRAMMABLE, DIGITAL VACUUM-OPERATED LIQUID SAMPLER

CROSS REFERENCE TO RELATED APPLICATION

This application claims the filing date of, and is based upon, prior U.S. provisional Patent Application Ser. No. 60/853,510, filed Oct. 20, 2006, and entitled Programmable Digital Vacuum Operated Liquid Sampler.

BACKGROUND OF THE INVENTION

I. Field of the Invention

The present invention relates generally to a bulk density sampling apparatus for continuously and repetitively measuring liquid samples from a bulk source and storing them for subsequent testing. More particularly, the present invention relates to a digitized, electronic liquid sampler that adaptively compensates and corrects for sampling errors.

II. Description of the Prior Art

Sampling devices have long been used under a variety of circumstances for collecting sample materials of both free flowing solids and fluids from various sources. For example, samples are routinely collected from waste water flow lines or reservoirs for subsequent testing and analysis. Many such devices provide for a sample pickup element to be fixed within the line of flow. Retractable sampling devices include hardware that is periodically inserted into the flow line and then withdrawn after the sample has been collected.

Prior U.S. Pat. No. 3,555,910, issued Jan. 19, 1971 to the instant assignee, provides a sampling apparatus for periodically withdrawing sample amounts of free flowing material from a continuous stream for testing. Such materials may be in a pressurized or non-pressurized tube, conduit or chute. The sample is obtained by extending a sample gathering apparatus into the tube or conduit capable of intercepting a portion of the moving material and then retracting the sample. The removal of the sample from the sampling device is accomplished by a controlled blast of air under pressure to move the material into an appropriate sample collecting container. This sampling apparatus is usable with free flowing granular material such as grain and the like and also with fluids.

A significant problem with prior art samplers that utilize suction techniques for withdrawing liquid samples is sampling errors caused by delays between suction shutoff instructions, relayed by the electronics, and the cessation of sampling intake. For the resultant sample to match that requested by a user, the software must make adaptive corrections to insure that the correct sample mass or weight is obtained, notwithstanding the delays occasioned by vacuum suction transfer techniques.

SUMMARY OF THE INVENTION

This invention provides a digital, programmable wastewater sampler capable of producing numerous sequential real-time samples from wastewater moved into and out of the system with vacuum. An adaptive algorithm is employed to correct the sample, repeatedly introducing a correction factor to insure that the measure mass after sampling approximates the mass inputted by a user.

The programmable device utilizes a highly reliable vacuum pressure pump rather than less-reliable, peristaltic pumping designs. Samples are fed into a measuring chamber, for digital analysis and measurement, prior to being transferred to a remote container for later analysis. A computer-controlled load cell within the chamber provides the initial sampling data. The invention combines a vacuum lift technique, a real-time mass measuring technique, and a software process for adaptive sample size feedback which allows repeatable, accurate sampling. Vacuum lift technology has several intrinsic benefits over peristaltic pumps; however, it has traditionally also suffered from lack of repeatability. This invention compensates for the lack of repeatability while leaving the advantages in place.

The sampler is characterized by numerous programmable parameters. For example, the time delay between sampling cycles can be varied. The sample quantity gathered during each cycle can be changed as well. The sample volume (i.e., in milliliters) to be gathered in each sampling cycle is thus user programmable.

The described pumping system is superior to peristaltic pumps because it moves the product without pinching the tubing that it goes through. Thus, it does not disturb or crush possible solids that may be suspended in the sample. It is also superior because the peristaltic system creates more wear on the intake tubing which can cause variances in sampling accuracy and requires scheduled maintenance more often. The discharge from the measuring chamber also leaves the tubing wide open as the sample passes through, leaving our system with a ⅜" (ID) intake and outlet system throughout without restrictions which peristaltic pumps cannot offer. Our measuring system does not require any sensors for actually make contact with the product, instead digitally measuring the sample.

Thus a basic object is to provide a programmable, digitally controlled sampler device.

A related object is to digitally analyze multiple, sequential samples.

A related object is to provide a sampler of the character described in which the time delay between sampling cycles can be varied.

A further object is to provide a sampler in which vacuum lift technology is coupled with real-time measurement and adaptive feedback to ensure accurate and repeatable sample sizes.

An important related object is to provide a software controlled liquid sampler that automatically corrects the obtained mass of vacuum-derived samples.

It is also an object to provide a sampler in which the quantity of liquid sample gathered during each cycle can be varied as desired by the user.

Another important object is to maximize reliability by extending tubing life. It is a feature of our invention that a vacuum system is employed, rather than a peristaltic pump, so the tubing through product movers is not degraded over time.

A related object is to provide a sampling system of the character described that does not deform or crush entrained solids traveling through the tubing.

A further related object is to provide a sampling system of the character described that has all of the advantages of vacuum lift systems while avoiding the traditional drawbacks.

These and other objects and advantages of the present invention, along with features of novelty appurtenant thereto, will appear or become apparent in the course of the following descriptive sections.

BRIEF DESCRIPTION OF THE DRAWINGS

In the following drawings, which form a part of the specification and which are to be construed in conjunction there-with, and in which like reference numerals have been employed throughout wherever possible to indicate like parts in the various views.

DETAILED DESCRIPTION OF THE PREFERRED EMBODIMENT

The instant liquid sampler repetitively suctions a liquid to be sampled, i.e., waste water, from a remote source. For example, samples may be obtained from a conventional sewage wet well buried in the earth. The automatic wastewater sampler combines a vacuum lift technique with real-time mass measurement and adaptive feedback logic to enable accurate, repeatable sampling heretofore unachievable with traditional vacuum lift techniques. This invention, therefore, has all of the advantages of vacuum lift while avoiding the traditional drawbacks.

Figure 1:
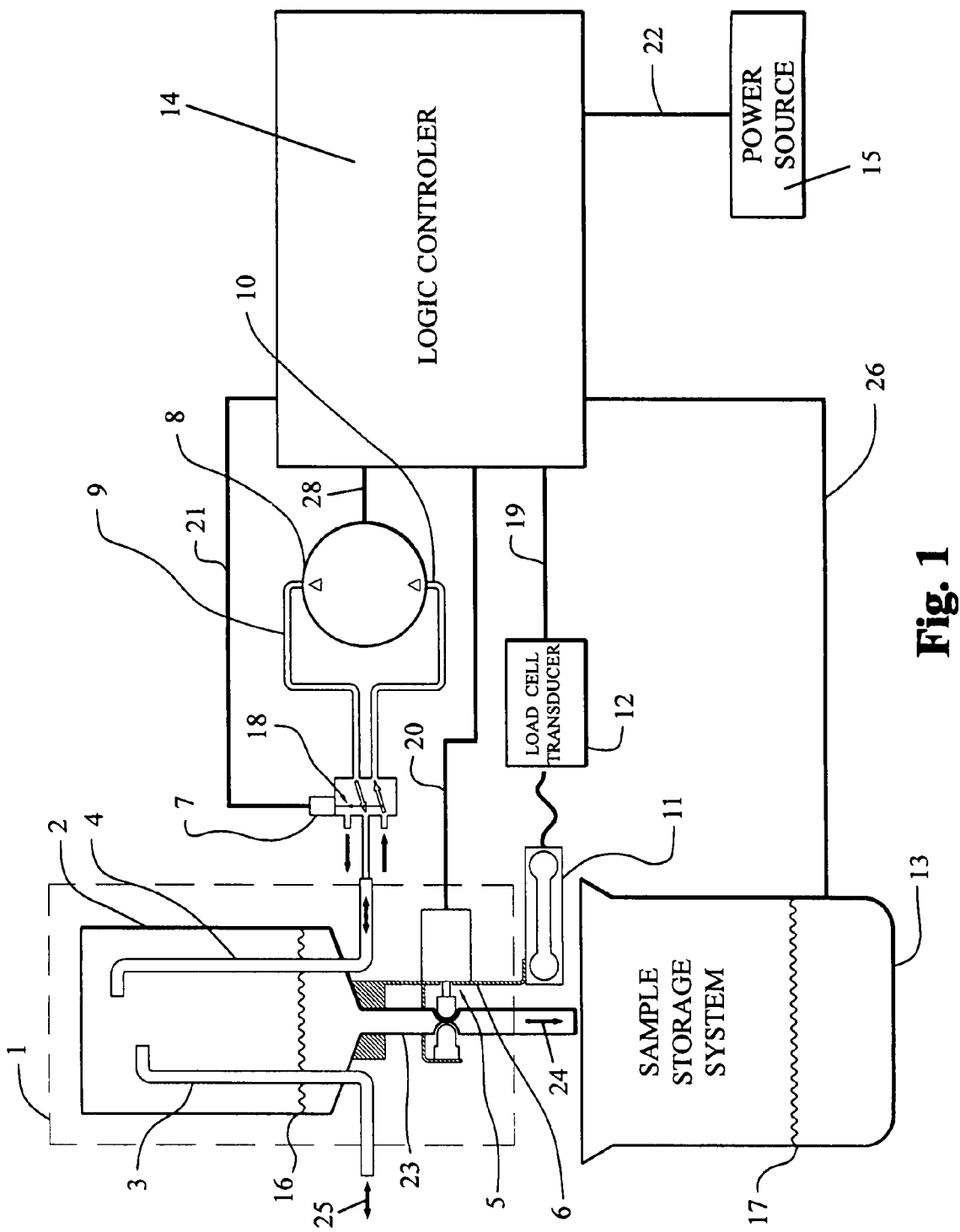
FIG. 1 is a functional diagrammatic block diagram illustrating the overall system concept of the preferred embodiment.

Referring initially to FIG. 1, a sampling assembly 1 comprises a sampling chamber 2, a sampling intake port 3, an air port 4, a discharge port 23, a pinch valve 5, and a mechanical coupling 6 that contacts the load cell. The sampling chamber 2 in the first preferred embodiment illustrated in FIG. 1 comprises a plastic cylindrical housing which screws onto a cylindrical plastic base and joins with a water-tight seal.

The sampling intake port 3 receives a sample drawn into the sampling chamber 2 under vacuum. In the preferred embodiment intake port 3 comprises an elongate plastic tube that receives liquid as indicated by arrow 25. The intake tube for port 3 enters sampling chamber 2 through the lower plastic cylindrical base and extends vertically to a point above the highest wastewater level 16 in the sampling chamber 2. This vertical height is chosen so that the sample, once in the sampling chamber 2, cannot exit the chamber through the sample intake port 3. As indicated diagrammatically by arrow 25, a sampling tube attached to the bottom of the sampling intake port 3 conducts a liquid sample from the source to be tested. The air port 4 alternately applies vacuum or pressure to the sampling chamber 2. Similar to the sample intake port 3, the air port 4 in the preferred embodiment consists of a plastic tube entering through the cylindrical plastic base and extending vertically to a point above the maximum wastewater level in the sampling chamber 2. As indicated diagrammatically, the bottom of the air port 4 is in fluid flow communication with a four-way valve 7 to be described hereinafter.

This discharge port 23 provides a path for a test sample, after analysis, to exit sampling chamber 2. In the preferred embodiment the discharge port 23 comprises a pliable, latex rubber tube. Pinch valve 5 functions as a switch, first retaining the sample within sampling chamber 2 and then providing a path for the sample to subsequently exit into sample storage system 13, as indicated by the vertical arrow 24, eventually establishing liquid level 17. Pinch valve 5 is controlled by logic controller 14 via line 20. System 13 (FIG. 1) generically represents both types of storage systems employed by the invention—composite and sequential. Composite storage involves a single container into which all the samples are deposited, such as that generally illustrated Sequential storage involves multiple bottles with the samples distributed between the bottles in a variety of ways depending on the programmed logic, as described later.

In the preferred embodiment the pinch valve 5 comprises an electrical solenoid, a plastic plunger, and a mating plastic anvil, the pliable discharge port 23 being pinched between the plunger and the anvil. The pinch valve 5 is just one means of alternately retaining and then releasing the sample. Alternate means could include pneumatic cylinders, commercially available valves, a sliding valve assembly among others.

The mechanical coupling 6 secures the sampling assembly 1 to the load cell 11, allowing real-time measurement of the mass of the assembly and the wastewater sample. In the preferred embodiment, the sampling chamber 2 and the pinch valve 5 are rigidly coupled and then attached to the measurement end of the strain beam of the load cell 11. The other end of the load cell 11 is rigidly attached to a fixed position in the sampler housing. As a practical consideration, the lines attaching the sample intake port 3 to the sample tube and the air port 4 to the four-way valve 7 should be routed in such a way as to minimize torque on the load cell during sample acquisition. Failure to do so can introduce significant measurement errors.

Air pump 8 supplies vacuum on line 10, and pressure along line 9 (FIG. 1). Vacuum or pressure are transmitted to the sampling chamber through the four-way valve 18 and air port 4. During sample acquisition, vacuum is applied to the sampling chamber 2 via air port 4 through a four-way valve 18. During sample discharge, pressure is applied to the sampling chamber 2. In the preferred embodiment, the four-way valve 7 comprises an electrical solenoid valve controlled by the logic controller 14 via line 21. Air pump 8 alternately functions as a vacuum means and a pressure means as selected by the logic controller 14 on line 28, combining both functions in a single device. Alternatively, vacuum and/or pressure could be generated in separate devices and separately controlled via the logic controller 14. Similarly the four-way valve 18 broadly functions as a switching means for alternately connecting vacuum or pressure to the sampling assembly 1.

The sampling velocity is the velocity of the material in the sampling tube 3 and subsequently the sampling port. Once the sampling material hits the sampling chamber, velocity is no longer an issue. Regulatory requirements fix the minimum linear velocity in the sampling tube 3 to prevent solids from separating during sample acquisition. This linear velocity is a function of the volumetric displacement of the air pump 8, the diameter of the sampling tube, the height difference between the sampling chamber 2 and the sample source, and sample viscosity. For very small sample sizes, excessive linear velocities may make sample acquisition less accurate; therefore, in some cases it is desirable to install a bleed valve or a fixed orifice in the pneumatic vacuum line 10 to introduce a calibrated leak, thereby reducing the linear velocity to an acceptable level.

During sample acquisition and prior to discharge, the mass of the sample is measured by the load cell 11 and the load cell transducer 12. In the preferred embodiment, the load cell 11 and the load cell transducer 12 form a modular assembly which communicates digitally over the peripheral communications bus 19 to the logic controller. This modularity was selected to allow the load cell 11 and the load cell transducer 12 to be calibrated separately at a factory independent of the logic controller. Also, a microcontroller embedded within the load cell transducer is used to offload processing power from the logic controller 14 providing better overall system response and hence better accuracy.

The load cell 11 and the load cell transducer 12 provide a measuring means whereby the sample mass is determined in real-time during sample acquisition. Alternate configurations could include a different method for determining either a direct measurement of mass or an indirect measurement of mass. Various techniques could be used for liquid level sensing, including ultrasonic techniques, capacitive techniques, optical techniques, and mechanical resonance techniques to name a few.

Importantly, vacuum lift technology is coupled with a real-time measurement and adaptive feedback to ensure accurate and repeatable sample sizes. Sample storage after acquisition and prior to collection for separate analysis is accomplished by storage system 13. Two storage systems are implemented in the preferred embodiment, composite and sequential. In the composite storage system all samples are deposited in a single container and mixed before analysis. In the sequential storage system samples may be deposited into a plurality of containers allowing samples to be segregated in one of several ways under logical control from the logic controller 14.

Logic controller 14 can be configured to store a single sample in each of a plurality of containers. It can store a plurality of sequential samples in a single container before indexing to the next container. It can store samples from a given hour of each day in a single container, thus grouping samples from the same time of day but across several days into a single container. Multiplicities of options are programmable. The important feature is that samples can be segregated logically into different containers. In the case of sequential sample storage, various control signals on line 26 (FIG. 1) are required between the logic controller 14 and the sample storage system 13. In the case of a composite storage system, no logic is required to be implemented physically between the logic controller 14 and the sample storage system 13.

Reference numeral 15 (FIG. 1) depicts a power source. In the preferred embodiment both AC and battery powered systems are implemented. AC systems are used in non-portable, fixed installations. Battery power is used in both portable systems and in fixed installations that require power loss failsafe operation. The logic controller 14 power subsection is designed to accommodate both AC and battery operations in a single device. Power is supplied via line 22 (FIG. 1).

Figure 2:
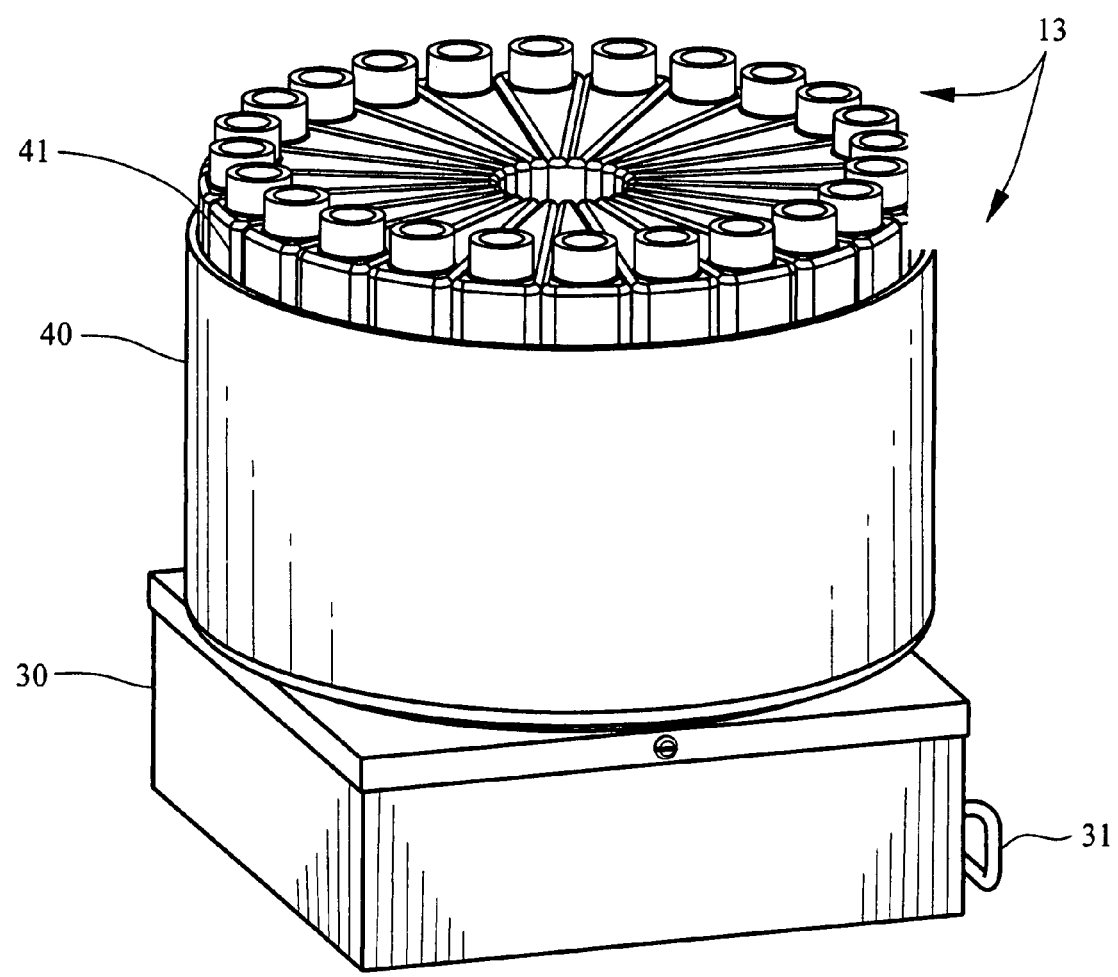
FIG. 2 is a perspective view showing the sequential sample storage carousel system employed with the preferred embodiment.

FIG. 2 shows the preferred sequential sample storage system 13. System 13 comprises a rotary table unit 30, connected to the logic controller via control cable 31, a generally cylindrical container carrier 40, and a plurality of sample containers 41. The sample containers fit within the container carrier 40 in a radial pattern. The number of containers is variable, and the container number can be a function of size and radial angle. Various model options exist for the sequential storage system. An example is a carrier with twenty-four, 500 ml. bottles. Another option is four separate one-half gallon bottles. The size of the bottles limits the number that can be radially distributed in the physical space.

Figure 3:
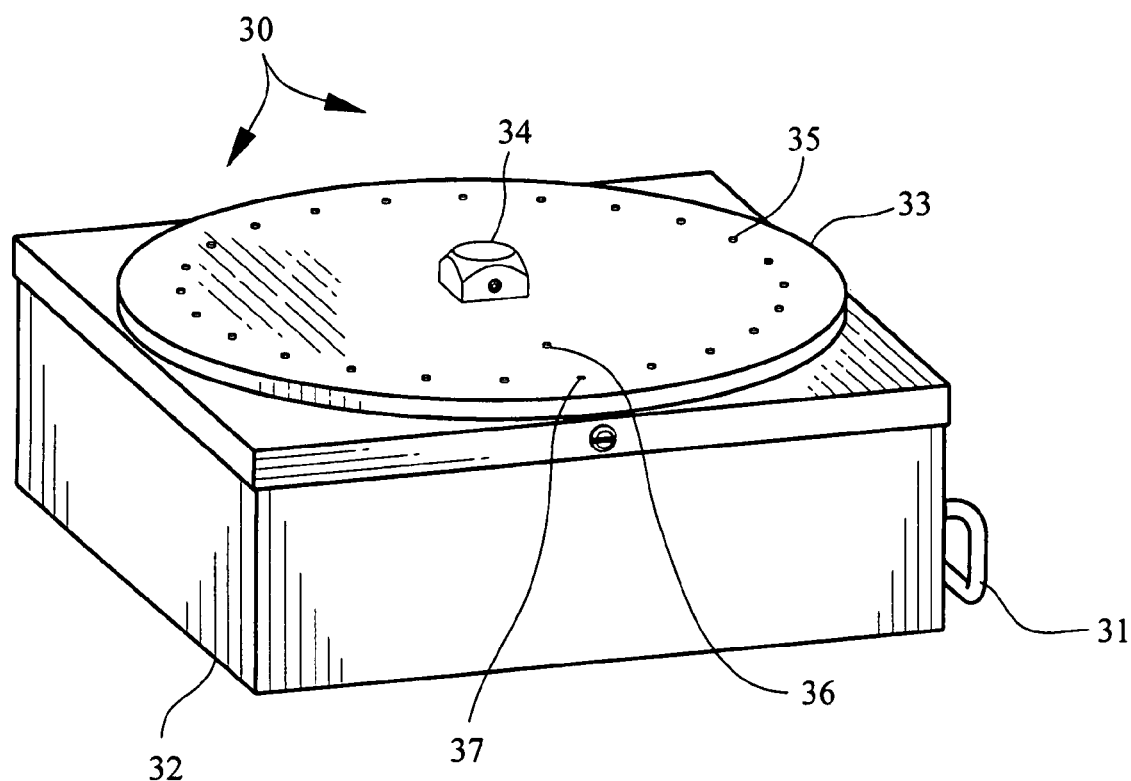
FIG. 3 is a perspective view illustrating the preferred rotary table employed with the sequential sample storage system of FIG. 2.
Figure 6:
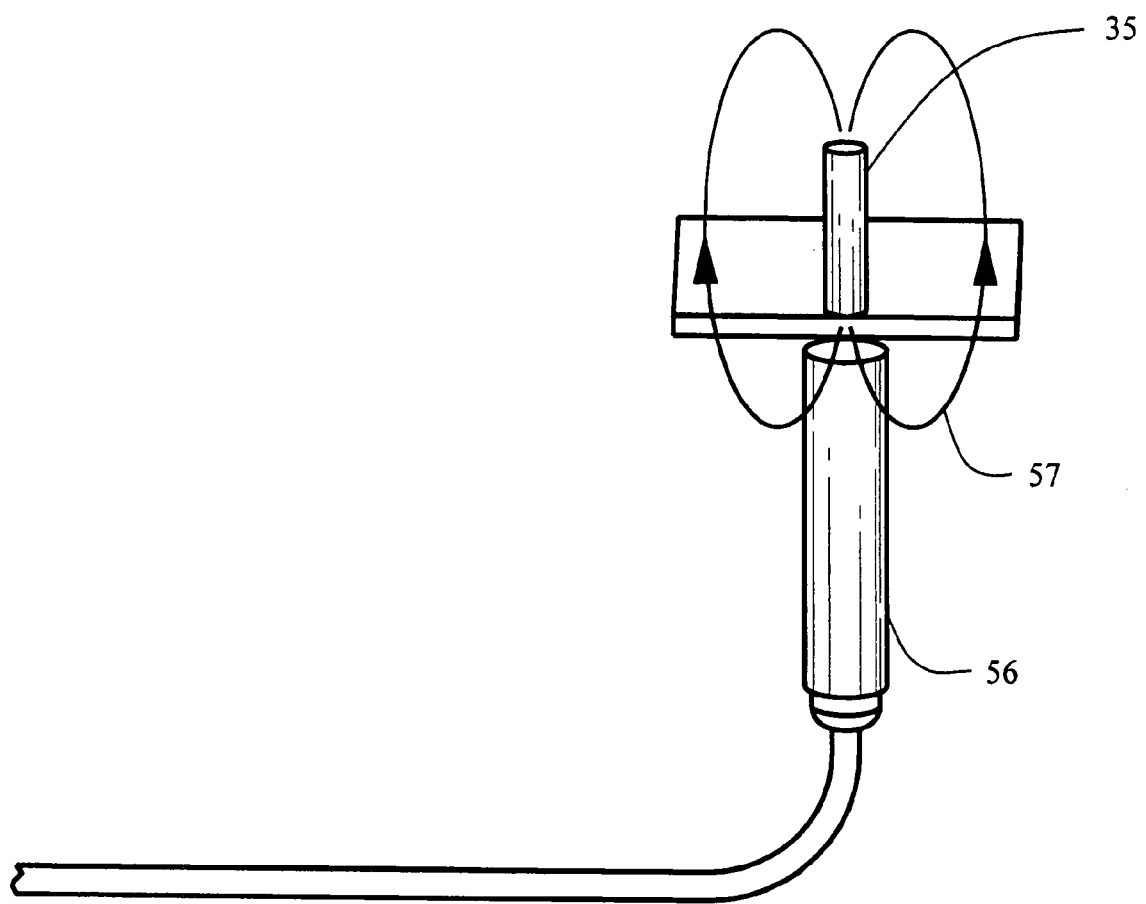
FIG. 6 is a diagrammatic view illustrating preferred index position sensing.

FIG. 3 shows the rotary table unit 30, which comprises a rotary table housing 32, containing a rotary drive motor and multiple (at least two) position sensors 35-37. The position sensors are preferably magnetic reed switches placed radially at a distance from the axis of rotation of the rotary table corresponding to the radii of the position indicated by 36 and 37. The magnetic reed switches are axially aligned with the axis of the position indicator magnets as shown in FIG. 6, and a circular, rotary platform 33 for supporting the container carrier 40. Platform 33 includes radially spaced apart index position indicators 35, a home position indicator 36, and 37. The centered index drive nut 34 (FIG. 3) mates with a socket (not shown) to rotate the cylindrical container carrier 40 (FIG. 2.

The index position indicators 35 and the home position indicator 36 (FIG. 3) preferably comprise cylindrical permanent magnets embedded within the plastic rotary platform 33. Magnetic index indicators 35 and 36 are sensed through the rotary table housing 32 by appropriately placed magnetic reed sensors 56 (FIG. 6) located beneath the upper surface of the table 33. The reed sensors 56 are radially distributed at the radii corresponding to position 36 and 37 and are axially aligned with the axis of the magnets. The upper surface of the rotary table housing is contained within the rotary table housing 32. The index drive nut 34 is designed to couple to a receptacle in the lower surface of the container carrier 40 keeping the angular relationship between the rotary platform 33 and the container carrier fixed, subsequently fixing the angular relationship between the rotary platform 33 and the individual sample containers 41. For a given container configuration within the container carrier 40, the position of the index position indicators 35 in the rotary platform 33 must correspond to the physical position of the containers 41 within the container carrier 40.

Figure 4:
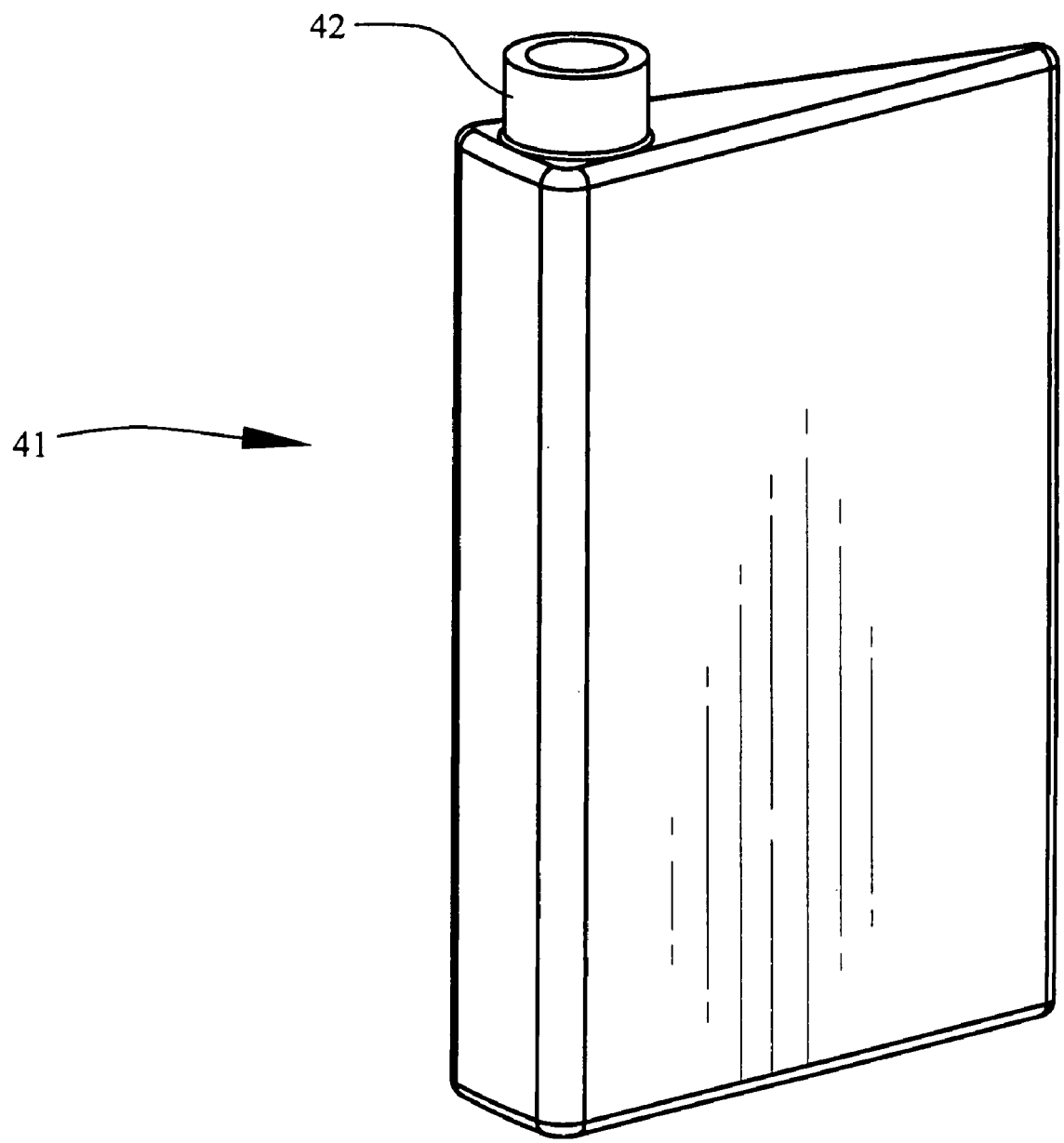
FIG. 4 is a perspective view illustrating a preferred sequential storage container employed with the invention.

FIG. 4 illustrates a typical sequential storage container 41 that is used with the preferred sequential carrier 40. A preferred, blow molded plastic container 41 is wedge shaped, and it comprises a cylindrical lid, attachment point 42. The lid attachment can be either screw type or snap on. Containers 41 each have a sector-shaped transverse cross section facilitating their radial deployment about the circular platform 33 as seen in FIG. 2.

Figure 5:
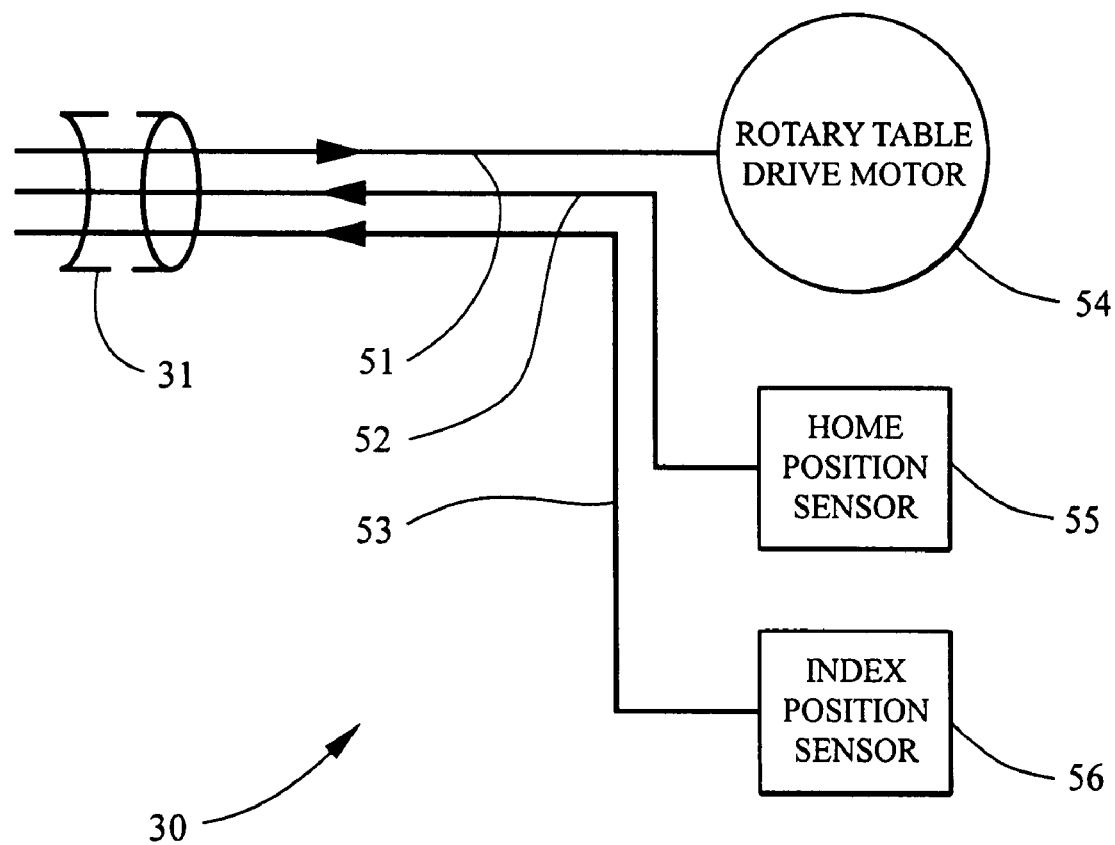
FIG. 5 is a functional block diagram illustrating operational functions of the rotary table of FIG. 3.

FIG. 5 shows the control functions within the rotary table assembly 30. A rotary table drive motor 54 receives a signal from the logic controller 14 via line 51. When activated, the rotary table drive motor will turn the rotary platform at a fixed rate. In the preferred embodiment motor 54 is a DC gear drive motor. The rotary table drive motor 54 (FIG. 5) may comprise a stepper motor, an AC synchronous motor, a servo system, or a ratchet-paw technique involving both solenoid or pneumatic techniques known in the art. The home position sensor 55 communicates to the logical controller 14 via control line 52 when the home position indicator is aligned with the home position sensor 55. Similarly, the index position sensor 56 communicates to the logical controller 14 via control line 53 when an index position sensor is aligned with the index position sensor 56. Sensors 55 and 56 are preferably reed switches, but they could be Hall-effect sensors, inductive proximity sensors, capacitive sensors, optical sensors, etc.

Technically, reference numerals 55 and 56 represent the sensing function not the physical hardware. Lines 51-53 run within control cable 31.

FIG. 6 illustrates the magnetic coupling between the index position sensor 56 (i.e., a reed switch within table housing 32 of FIG. 3) and the index position indicator 35 on rotary platform 33 (FIG. 3). The magnetic flux lines from the index position sensor 35 are coupled into the index position sensor 56 as shown by reference numeral 57. It will be clear to those skilled in the art that a number of sensor/indicator technologies could be used to achieve the same performance including optical techniques, inductive proximity sensor techniques, capacitive sensor techniques, hall-effect sensor techniques and mechanical switches. Similarly, the sequential storage system could have been linear storage as compared with the described radial system. Such design variations are anticipated within the scope of this invention.

Figure 7:
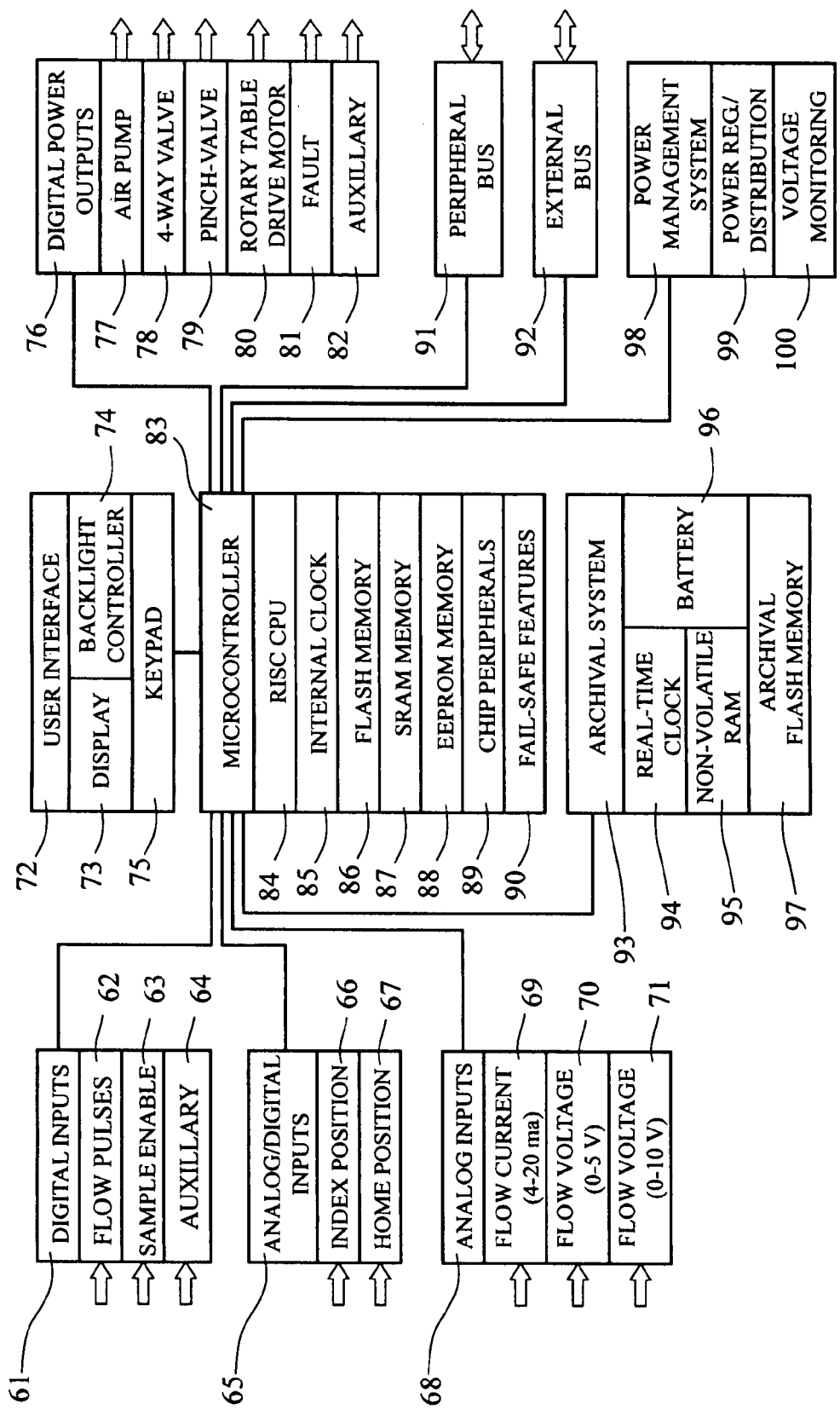
FIG. 7 is a functional block diagram of the preferred logic controller of FIG. 1.

FIG. 7 illustrates major electronic features of the logical controller 14. The control logic is preferably implemented using a Harvard Architecture FLASH based RISC microcontroller 83. The microcontroller major subsystems include the RISC CPU 84, the CPU clocking system 85, FLASH based program memory 86, SRAM based data memory 87, internal data EEPROM 88, various chip peripherals 89, and various built-in fail-safe features 90. In the preferred embodiment, the Harvard Architecture provides for separate data and program memory spaces. Code for the microcontroller is written in a combination of assembly language and ANSI C. The CPU clocking system 85 is capable of being generated from a plurality of sources, but the design implements a primary clock from an external crystal for accuracy reasons. Internal software clocks are all derived from this external crystal source. Typical microcontrollers suitable for this design have a plurality of on-chip peripherals. At a minimum this design requires two asynchronous serial ports (UARTS), various internal hardware clocks capable of generating interrupts, multiple analog to digital conversion channels, and configurable digital I/O. The fail-safe feature 90, implemented in this design, include a hardware based internal watch dog timer and brown out detection circuitry.

The user interface 72 (FIG. 7) comprises a graphic LCD type display 73 with variable intensity backlight control 74 and a keypad 75. The keypad 75 consists of 10-digit numeric entry keys, a backspace key, an enter key, up and down scroll keys, and three soft keys associated with three zones on the LCD display 73. The soft keys are used for activating multiple functions depending on the context of the running program. The content on the LCD display 73 in the display zones associated with the soft keys changes depending on the context of the program. These softkeys are primarily used for menu navigation during user configuration and for context switching during sample program execution. The logic controller 14 (FIG. 1) also implements a long term archival feature for logging events during the life of the product. Typical logged events include sample acquisition, program start and stop events, exception events, program changes, power outages, and system resets among others.

The archival system 93 (FIG. 7) consists of external archival FLASH memory 97, a real-time clock 94, non-volatile RAM 95, and a battery 96 for backup of the real-time clock 94 and the non-volatile RAM 95. The real-time clock 94 provides a time of day and date time stamp for the archival records in the archival FLASH memory 97. The non-volatile RAM 95, though included in the archival system hardware, also serves to store rapidly changing program state data in the event of a power failure. This data is used to restore the system to its last state prior to the loss of system power. Three types of non-volatile storage are provided in the logic controller: the non-volatile RAM 95, the EEPROM memory 88, and the archival FLASH memory 97. These three memories have differing characteristics and are used in a complementary fashion to support the fail-safe operation of the logic controller. The non-volatile RAM 95 has rapid write capabilities and an unlimited number of read/write cycles. The data EEPROM 88 has a larger memory size and has rapid read capabilities, but quite slow data write times. It is byte writable. The archival FLASH memory has a much larger memory space, but is not byte writable. It also has a very limited number of write cycles.

Given their different characteristics, the three memories 95, 88 and 97 (FIG. 7) are used for three distinctively different purposes. The non-volatile RAM 95 is used for rapidly changing system state variables. It is typically updated every second during program execution. The data EEPROM is used for system configuration variables, sample program configuration, and for logging data associated with individual samples and sample containers during a sampling program execution. A plurality of sampling programs can be configured by the user to determine when to sample and what to do with each sample. The archival FLASH memory 97 is used for logging rather long records associated with archival events. It performs much like a very large circular queue with the most recent data always being loaded and the oldest data being erased when the memory is full. The size of archival FLASH memory 97, however, is sufficiently large that several years of typical operation are capable of being stored without loss of data. All three types of non-volatile memory are checked for corruption using cyclical redundancy checks (CRC) at the record level. Each record, prior to being written has a 16-bit CRC calculated and appended to the record. On reading, each record is verified using the same CRC calculation to check for errors. This ensures that if a write is interrupted and does not complete correctly that the corrupted_data is not subsequently used in error. Power regulation features are indicated by block 99. Further voltage monitoring, as indicated by block 100 in FIG. 7, is done prior to most writes to ensure that the write will be capable of being successfully completed.

The logical control 14 implements a variety of inputs including analog inputs 68 (FIG. 7), the combination analog and digital inputs 65, and high-level digital inputs 61 (FIG. 4). The analog inputs 68 and the digital inputs 61, and flow pulses 62 are used under configurable program control to determine the appropriate time for acquiring a sample. Sampling programs can be configured by the user through a series of menus to determine when to take a sample. Sampling can be variably configured to take place at a specified time, at a variable list of times, at a specified flow, at a variable list of flows, and at a combination of times and flows. The time base for sampling is derived from the internal clock 85 in conjunction with timing hardware provided by the chip peripherals 89. The flow signal is derived from one of four sources: the digital input flow pulses 62, the flow current 69, the zero to five volt flow voltage 70, or the zero to ten volt flow voltage 71. This is configurable under software control and is stored in the non-volatile sampling program records in the data EEPROM 88. If "flow pulses 62" is selected, the sampling interval is related to a number of pulses on the flow pulses 62 input. Hardware protections are provided on this input and all the digital inputs 61 to protect against electronic damage due to over voltage conditions. Software filtering is provided to protect against spuriously detecting noise as pulses. This software filtering is matched to the pulse rates that are common in flow sensors used in the industry. If one of the analog inputs 68 is selected, the user can select the sampling interval using a simple procedure. The user is asked to input the maximum flow rate of the sensor and then is asked to input the total flow between samples. The scaling and interval calculations are performed by the logic controller. This simplification is an advantage over prior art solutions, which require the user to calculate the scaling factors manually. 66 67

The analog inputs 68 (FIG. 7) all share a common connector on the printed circuit board. The input type is selected via software for one of the following four to twenty ma. current loop 69, zero to five volt full scale signal 70, or zero to ten volt full scale signal. The combination analog/digital inputs 65 accept the signals from the rotary table assembly 60. These will accept either a digital signal or a current loop four to twenty ma. signal so that a variety of sensors could be used in the rotary table assembly 60. The two inputs 66 and 67 correspond to the logical signals 52 and 53 on FIG. 5.

The digital input, sample enable option 63 (FIG. 7), is used with sampling programmable options to allow an external float switch, or similar device, to signal the sampling program to change states. The actual logic of this input is program dependent and firmware dependent. An auxiliary input 64 is provided to allow additional functionality in future generations of the design. All inputs groups 61, 65, and 68 are designed to survive incorrect wiring and industrial or commercial ESD events.

Six digital power outputs 76 (FIG. 7) are provided in the logical controller 14. Each of these consists of an appropriately sized relay and each supplies power to its respective device in FIG. 1. The output air pump 77 is configured to drive both AC and DC air pumps with AC snubbing and DC flyback protection integral to the configuration. The four-way valve 78 output is a relay configured to drive a twelve volt DC solenoid valve. Flyback protection on the contacts is provided. The pinch-valve 79 output is a relay configured to drive a twelve volt DC solenoid. Flyback protection on the contacts is provided. The rotary table drive motor 80 output is a relay configured to supply twelve volts DC to the rotary table drive motor 54. Again, flyback protection on the contacts is preferred. The fault 81 output is a relay providing a set of dry contacts to downstream logic in the event of a failure to sample or other fault condition. The use of this relay is optionally configurable under software control. The auxiliary output 82 is a relay providing a set of dry contacts for downstream logic. It is included for future functionality, but presently signals the presence of a sampling cycle.

Two data buses (FIG. 7) are provided for communication with other systems. The peripheral bus 91 is included for communicating with the load cell transducer 12 and future sensors. It is hardware configured to be compatible with the SDI-12 industry standard, but can under software control, communicate via a proprietary protocol. The external bus 92 is an RS-232 compatible serial bus for communicating with a PC or other data collection device primarily intended for downloading the archival data. It can optionally be programmed as a configuration and factory test port. The logic controller 14 further incorporates a power management system 98. This is used for two primary purposes: power regulation and distribution about the various board subsystems and voltage monitoring to detect battery levels and/or an AC power loss condition. This system is used to conserve battery power and to detect conditions which could corrupt non-volatile memory storage routines.

Figure 8:
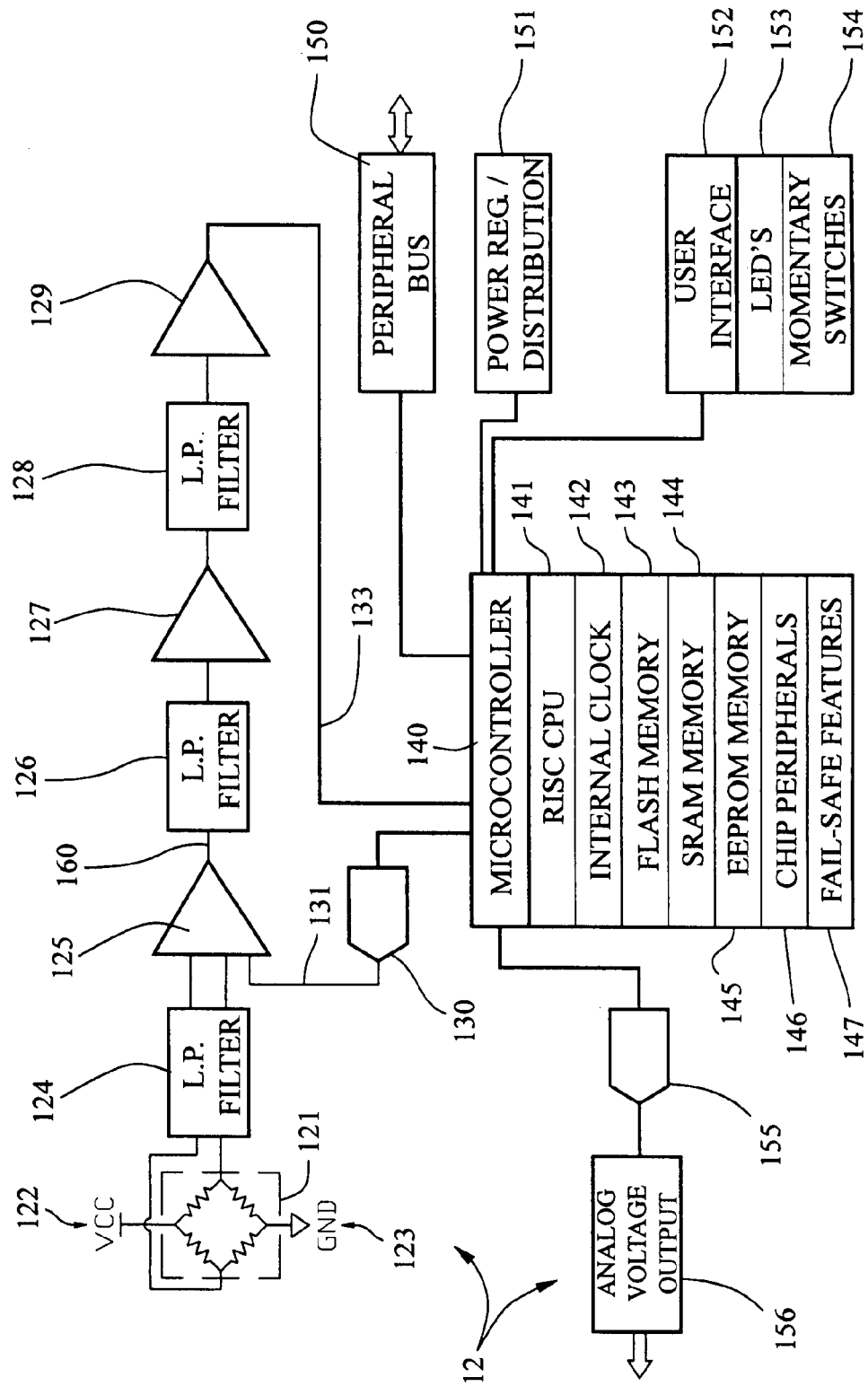
FIG. 8 is a functional block diagram of the load cell transducer of FIG. 1.

Referencing FIGS. 1 and 7-8, the preferred load cell transducer 12 is designed to communicate to the logic controller 14 via the peripheral bus 91 (FIG. 7). The load cell transducer can be calibrated independently of the logic controller 14, or in conjunction with the logic controller 14. The logical control of the load cell transducer 12 is accomplished with a FLASH based, RISC microcontroller 140 (FIG. 8). It comprises a RISC based CPU 141, an internal clock generating system 142, FLASH memory 143 for program storage, SRAM memory 144 for run-time variables, EEPROM memory 145 for non-volatile storage of calibration constants, a plurality of chip based peripherals 146, and a number of fail-safe features 147. The chip based peripherals 146 include a multiple channel ADC system for analog to digital conversion of the signal conditioned load cell voltage 131. Fail safe features of the microcontroller 140 include a watch dog timer and brown out detection circuitry. The load cell analog signal conditioning is accomplished via a multiple stage filter/amplifier system.

Each side of the differential signal from the load cell 121 is derived through the bridge circuit, between Vcc and ground, respectively indicated as 122 and 123. That signal is first passed through a simple single pole low pass filter 124 prior to being routed into a first input of differential instrumentation amplifier 125. The output from the differential instrumentation amplifier 125 is passed via line 160 through a single pole low pass filter 126 prior to being scaled and offset in the fixed gain amplifier 127. A third low pass filter 128 further filters the signal prior to final buffering in the amplifier 129, which feeds its output directly into an ADC input on the microcontroller 140 via line 133.

A feature of the analog signal conditioning (FIG. 8) is a wide range zeroing function. Input line 133 on the instrumentation amplifier 125 is used to change the offset voltage of the instrumentation amplifier 125. The microcontroller 140 controls the subcircuit 130. Under software control, circuit 130 can deliver a range of voltages to the second input of differential amplifier 125 on line 131. This voltage is what alters the span adjustment on the amplifier and provides a closed-loop between the microcontroller and the analog sensing circuit allowing a measurement window to be variably moved across a wide range of input masses. Thus, the effective zero point of the load cell can be varied over the entire range of the load cell. The gain of amplifiers 125, 127 and 129 determine the full-scale range of the load cell 121, but the voltage at 131 determines the zero point. In this way, a measurement window with rather high resolution can be moved over a large range of overall voltages. This allows, for example a one-thousand gram range with a resolution of one gram to be selected from a total range of ten-thousand grams.

The software zeroing function is critical to the overall operation of the automatic sampler. First, it allows rather large range load cells to be used which are less susceptible to mechanical damage. Secondly, and more importantly it allows a rather precise measurement to be made in the presence of a relatively massive assembly. Thus, the sampling assembly 1 can vary considerably in manufacturing and the load cell transducer 12 is capable of handling those variations. Thirdly, this allows zeroing of the measurement prior to taking a sample so that an accumulation of debris in the sampling chamber 2 has no effect on the individual sample accuracy.

In the preferred embodiment a variable calibration ability thus results. The microcontroller controls the variable voltage source 130 (FIG. 8) and in doing so is able to move the measurement window across a wide range of masses. In effect this is the "tare" function on an electronic scale. The voltage on line 131 (FIG. 8) can also be varied with a digitally controlled potentiometer and an operational amplifier. Other techniques could have been used including, but not limited to, a DAC, pulse width modulation with output filtering, and a frequency to voltage converter.

The load cell transducer 12 has two user input switches 154 and two user LED's 153 which under software control can be used to both zero the load cell and calibrate the load cell against a reference mass. Its user interface is designated with the reference numeral 152. The calibration factors are then saved in the EEPROM memory 145 so that the output is scaled appropriately after power loss. This allows the load cell 11 and the load cell transducer 12 to be calibrated in a stand-alone environment prior to shipping from a factory. The load cell transducer derives its power from the peripheral bus 150, but local voltages are regulated on the load cell transducer PCB. This regulation and distribution function is represented by reference numeral 151. The peripheral bus interface 150 is hardware compatible with the SDI-12 industry standard, but communicates preferentially with a customized protocol. The SDI-12 standard is referenced, for example, in "*A Serial-Digital Interface Standard for Microprocessor-Based Sensors*, Version 1.3, Jul. 18, 2005, Prepared by SDI-12 Support Group (Technical Committee), 165 East 500 South, River heights, Utah (http://www.sdi-12.org).

A UART on the microcontroller 140 is used for communications functions. Power is delivered to the load cell by the peripheral bus 150 (FIG. 8). This power can be switched on and off under control from the logic controller 14. When power is applied, the microcontroller 140 experiences a power on reset. The various systems are initialized and the calibration constants are retrieved from the EEPROM 145. The load cell parses the commands originating from the logical controller that are delivered over the peripheral bus interface 150, executes those commands, and responds accordingly. Example commands are, but not limited to zero the load cell, calibrate the load cell, read the load cell, and notify when a preselected mass is reached. The command to notify the logic controller when a preselected mass is reached allows the load cell transducer 12 to off-load significant processing power from the logic controller 14 while a sample is being acquired. 152 153 154

Figure 9:
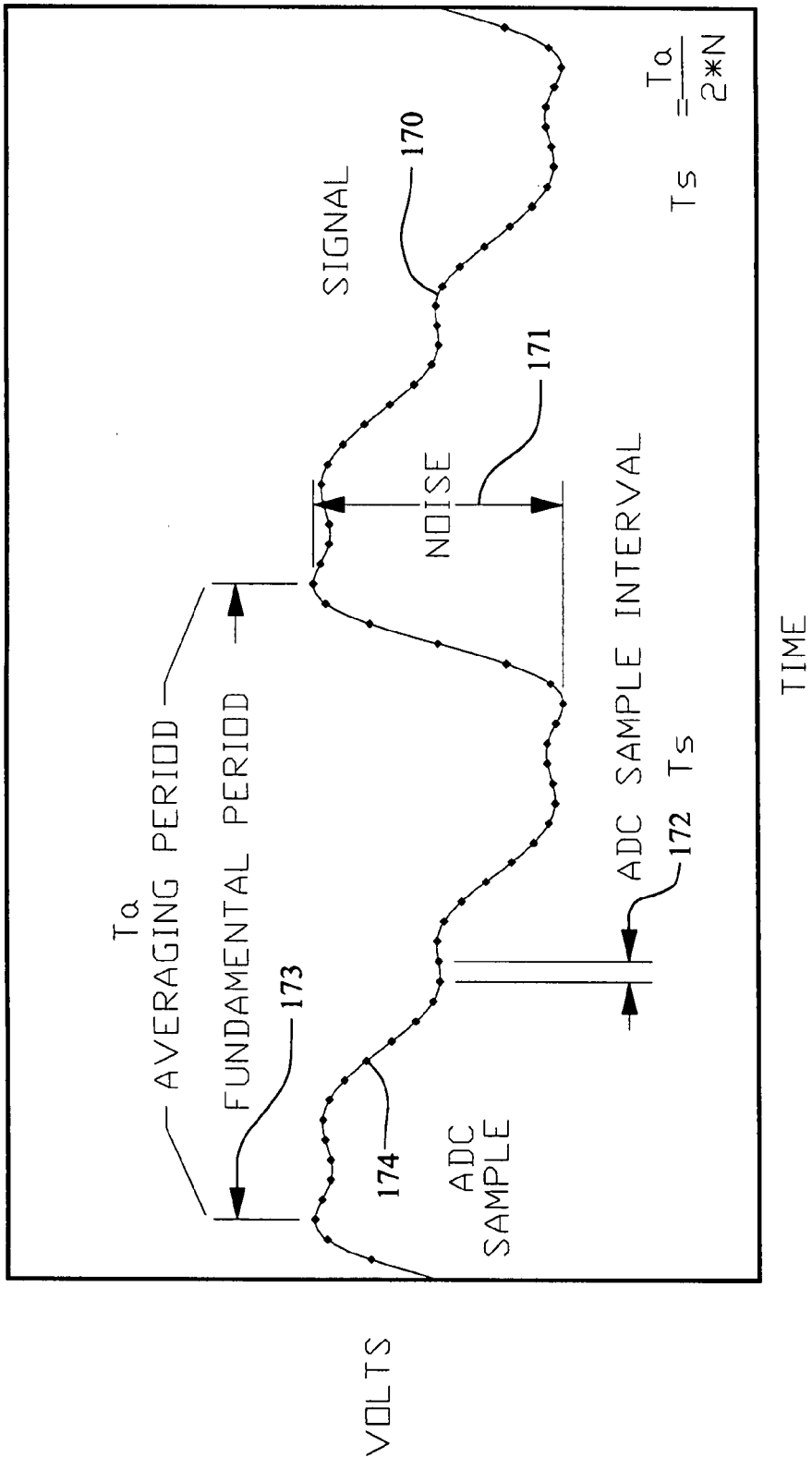
FIG. 9 is a graph depicting the preferred load cell signal process, with voltage plotted against time.

In conjunction with the described vacuum lift technique mechanical vibrations result from the close coupling of the air pump 8 with the base to which the load cell 11 is mounted. When the air pump 8 is running, which is always the case during sample acquisition, mechanical vibrations coupled into the load cell can introduce a periodic noise that is significantly larger than the resolution of the signal under consideration. FIG. 9 illustrates this. If a probe were placed in the load cell circuitry on line 160 in FIG. 8, the observed signal would look similar to signal 170 in FIG. 9. The noise amplitude 171 (FIG. 9) is in the order of 30% of the entire load cell range. The sample interval is designated 172. The ADC sample waveform is 174.

Referencing FIG. 9, 170 the analog signal that would be measured if an oscilloscope were place at location 160 in FIG. 8 is numbered 170. Sample point 174 represents a digital sample taken in time along this analog signal, this distinction is important. The continuous analog signal is 173, 174 is the digitized sample used in the digital algorithms.

For example, if a one thousand gram range is under consideration, then the noise generated (i.e., 171 in FIG. 8) at the load cell due to mechanical vibrations could be as much as three hundred grams. The sampling interval is designated 172. This noise is superimposed on the actual mass value which must be acquired with a resolution of approximately one g. The low pass filters 125, 127 and 129 (FIG. 8) in the load cell analog signal conditioning circuitry can be used to minimize the noise, but these introduce an alternate problem. If the signal is over filtered, then the response time of the measuring system is reduced such that the mass of the sample under acquisition is predicted too low in real-time. If the delays to recognize the sample weight are significant, then the acquisition will overshoot and the sample will be acquired with significant error. Similarly, if the signal is under filtered, then the noise amplitude will terminate sampling too soon and the sample will be less than the target mass.

Proper filtering (i.e., FIG. 8) remedies the latter problem. A filter with a pure zero gain at a specific frequency is preferred. That is, if none of the frequency is passed by the filter, then this is a pure zero. An analysis of the noise signature in the design shows a common fundamental noise frequency with variable amplitude harmonics. The fundamental period is shown by reference numeral 173 in FIG. 9. It is recognized that a boxcar averager properly designed has a pure zero at the fundamental frequency and several of the harmonic overtones. The ADC conversion was synchronized to collect $2^n$ samples in each fundamental period 173. By averaging these samples, n overtones can be purely rejected. This boxcar averager, coupled with properly selected low pass cutoff frequencies in filters 125, 127 and 129 (FIG. 8) allows the signal to be measured accurately and with optimal time response. Furthermore, the load cell transducer may use logic to extrapolate and predict the point in time when the sample mass will be collected. As the signal gets close to the target value, the firmware looks to see if the signal is closer than the time period represented by the 2 to the nth samples comprising the boxcar averager. If the signal is closer than the change in the signal between the last two averaged samples then it calculates the time at which the target should be reached based on the last rate of change. It interpolates the time based on the last known rate of change.

Figure 10:
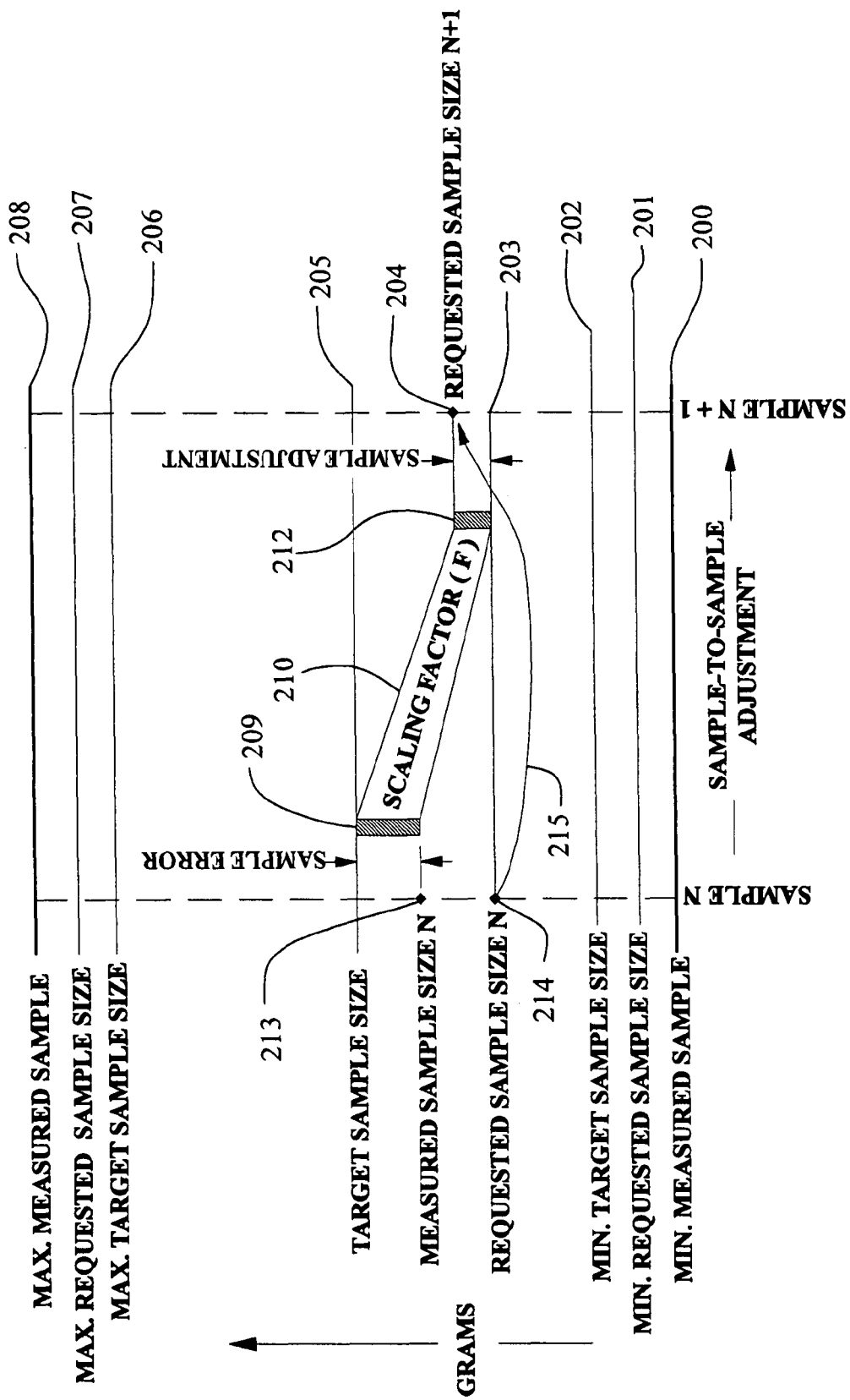
FIG. 10 is a diagrammatic view illustrating the preferred adaptive feedback process for sample-to-sample mass correction.

With reference directed jointly to FIG. 10, there is a desired target sample size 205, a requested sample size 214 determined and suctioned in by the sampler, and then, after sample acquisition, a measured sample size 213 results. As used herein, the "Target sample size" is the size of sample that the user programs into the sampler. The "Requested sample size" is the size of sample that is actually requested by the sampler electronically to the load cell, and it ultimately depends on the adaptive feedback. The "Measured sample size" is a measurement of what was drawn into the system by suction, and it's value is used to improve the next requested sample size. The adaptive logic transforms a first requested sample size 214 (FIG. 10) into a corrected size 204, as indicated by arrow 215. A scaling factor 210 is derived and applied as explained hereinafter. Size 204 is greater than the first requested sample size indicated at 214 and by line 203. The maximum target, requested and measures sample sizes are designated generally by lines 206, 207 and 208 (FIG. 10) respectively. The minimum target, requested and measures sample sizes are designated generally by lines 202, 201 and 200 (FIG. 10) respectively.

During sample acquisition, liquid is drawn through the sample intake port 3 (FIG. 1), through a height above liquid level 16, within the sampling assembly 1. Even before sample material is entering the sampling chamber, mass is being detected by the load cell transducer 12. After a sample begins to be injected into the sampling chamber (FIG. 1) the load cell transducer 12 determines that a machine-requested liquid mass has been acquired. This signals the logic controller 14 to reverse the state of the four-way valve 7 to begin to pressurize the sampling chamber 2. This switching time has a small but measurable delay. There is a similar delay as air begins to pressurize the sampling chamber 2, and, thus, the resultant mass will typically overshoot the mass measured at the time that sample intaking was logically terminated. This coupled with delays due to signal response time in the sample measuring system require that some sort of adaptive feedback be included in the sampling system to accommodate the variations in configuration and temporal variations that occur during the draining of a system battery or slowly varying variations in AC line voltage. Requirements of the feedback system are that it must converge on the correct sample size quickly (within just a few sampling cycles), that it should not oscillate outside of the sampling accuracy specification when near the target sample size, and that excursions toward the sampling limits should not oscillate. The preferred embodiment implements a simple algorithm in which the subsequent sample is determined by the error in the previous sample. More sophisticated algorithms are possible within the scope of this invention, but this is preferred for simplicity and efficiency of microcontroller resources. The sample volumetric velocity is affected by a plurality of factors including but not limited to air pump displacement rate, sampling height, sample viscosity, volume of the sampling chamber 2, and remaining air volume in the system.

FIG. 10 diagrammatically illustrates the preferred adaptive feedback. For each Sample N, there is a desired target sample size 205 desired and inputted by the machine operator which is followed by a machine generated requested sample size 214 suctioned in by the apparatus. The mass of the resultant sample is measured as indicated by 213. Prior to taking the next sample, a sample error 209 (FIG. 10) is calculated as the difference between the target sample size 205 and the measured sample size 213. This error is multiplied by a scaling factor 210, designated "F". The resulting value 212 is added in the software to force the circuit to internally generate a new "requested" sample size 214 that will be sought in the succeeding cycle.

Figure 11:
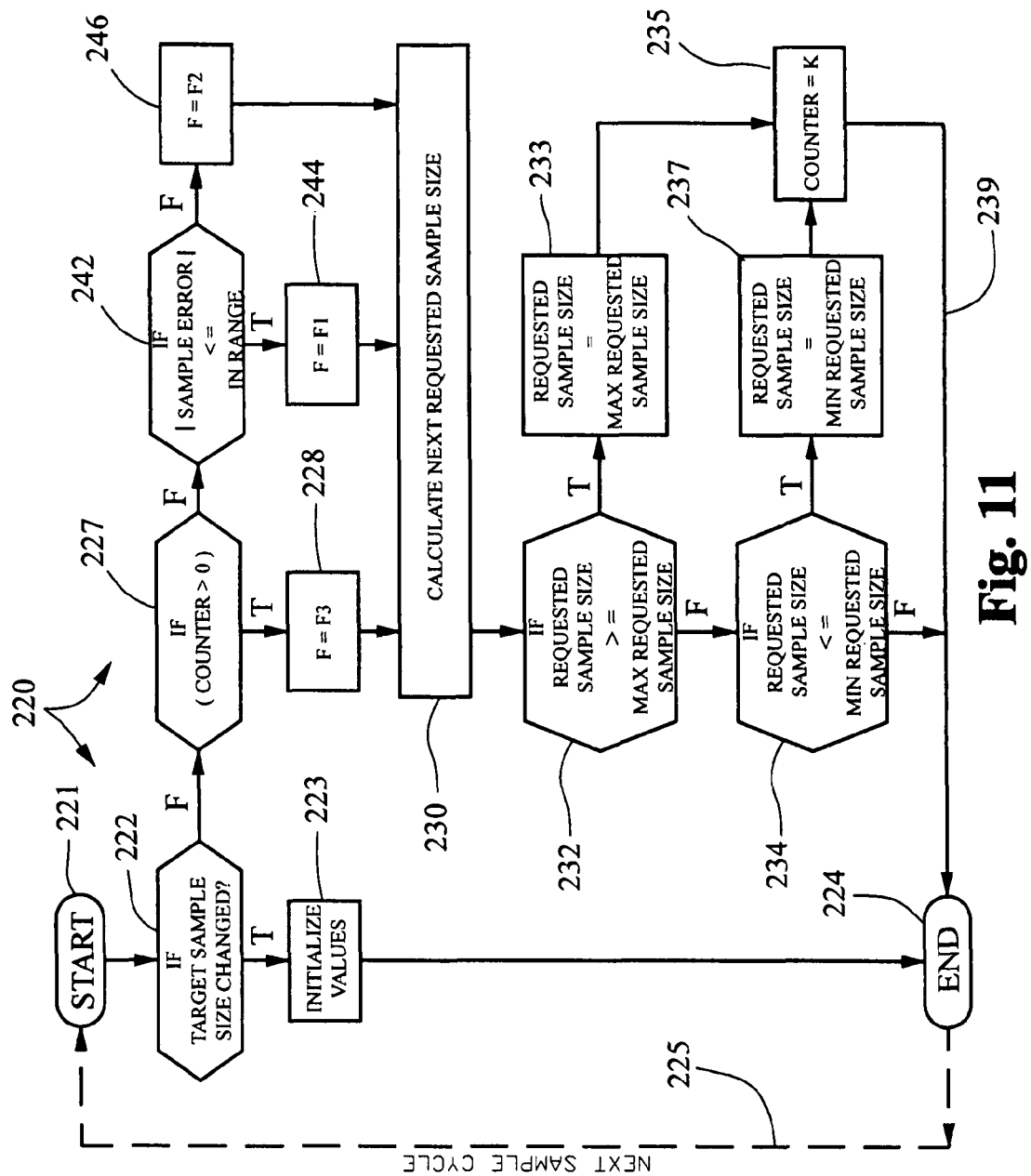
FIG. 11 is a software flowchart illustrating the logic for determining the scaling factor used in the adaptive feedback process of FIG. 10; and, FIG. 12 is a software flowchart illustrating the preferred processes involved in acquiring a single sample.

If the measured sample size 213 is sufficiently close to the target sample size, then F is relatively small. If the measured sample size is sufficiently far from the target sample size, then F is large to encourage rapid convergence. Simply stated, with each sample the requested sample size is adjusted by a fraction F of the error of the last sample. The scaling factor F is not constant, but is dependent upon where in the sample measurement range the measured sample lies. In FIGS. 10 and 11 the values for F1, F2 and F3 are determined by the parameters of the system, but are fixed with a given model. F2 is typically greater than F1. F2 is typically greater than F3.

Referencing primarily FIG. 11, the correction factor "F" and the combination of the load cell transducer signal conditioning/processing and the adaptive feedback logic are critical to the accuracy and the repeatability of the sampling system. FIG. 11 illustrates the adaptive logical process 220 for determining and generating "F." It is assumed that the user-selected target sample size 205 is constant within a program cycle. After program start step 221, step 222 determines if the target sample size 205 (FIG. 8) is changed, and, if so the system variables associated with the adaptive feedback are initialized in step 223 to values that have been empirically determined in the design. These values are based on experiments with typical sampling flow rates, the present sample chamber size and the present pump. It is an attempt to get at close as possible on the first requested sample size. The actual values are not so important, because they will change as more field experience is gained and/or the design is refined. The end step 224 is thus followed by a next sample cycle as indicated by line 225 when the cycle restarts and repeats.

If the calculated requested sample size is either too large in the measurement range or too small in the measurement range, then the requested sample size is limited to the two limits 201 and 207 (FIG. 10) and a counter is initialized. When close to the limits, there is a possibility of oscillation, so presently for five sampling cycles the convergence rate is limited by reducing the scale factor. The software counter 235 (FIG. 11) is what is keeping track of this period of reduced convergence. Acceptable results occur where K=5 but this value may be changed with software. For the next K samples, then the scaling factor "F" is reduced. This prevents oscillation at the extreme ends of the measurement range.

If step 227 (FIG. 11) determines that the counter step 235 (explained hereinafter) is greater than zero, step 228 sets "F" equal to "F3." The machine calculates the next requested sample size using the correction factor "F3" in step 230 utilizing the process of FIG. 10. In step 232 if the requested sample size recalculated in step 230 is greater than or equal to the maximum possible requested sample size limit 207 (i.e., FIG. 10) step 233 resets the requested sample size to the maximum allowed requested size 207 and counter step 235 follows. Conversely, in step 232 if the requested sample size recalculated in step 230 is not greater than or equal to the maximum requested sample size limit 207 (i.e., FIG. 10) step 232 is followed by step 234. If the requested sample size recalculated in step 230 is less than or equal to the minimum allowable requested size 201 (FIG. 10), step 234 is followed by step 237 that resets the requested sample size to the minimum allowed requested size 201, and the counter step 235 follows, outputting on line 239. The cycle repeats as indicated by dashed line 225.

If step 227 determines that the counter step 235 output is not greater than zero, step 242 is followed by step 244 to set "F" equal to "F1," and the calculation step 230 is followed by steps 232 and 234. If the sampling error is outside the range of step 242, step 246 sets "F" equal to "F2," and calculation step 230 again follows.

Figure 12:
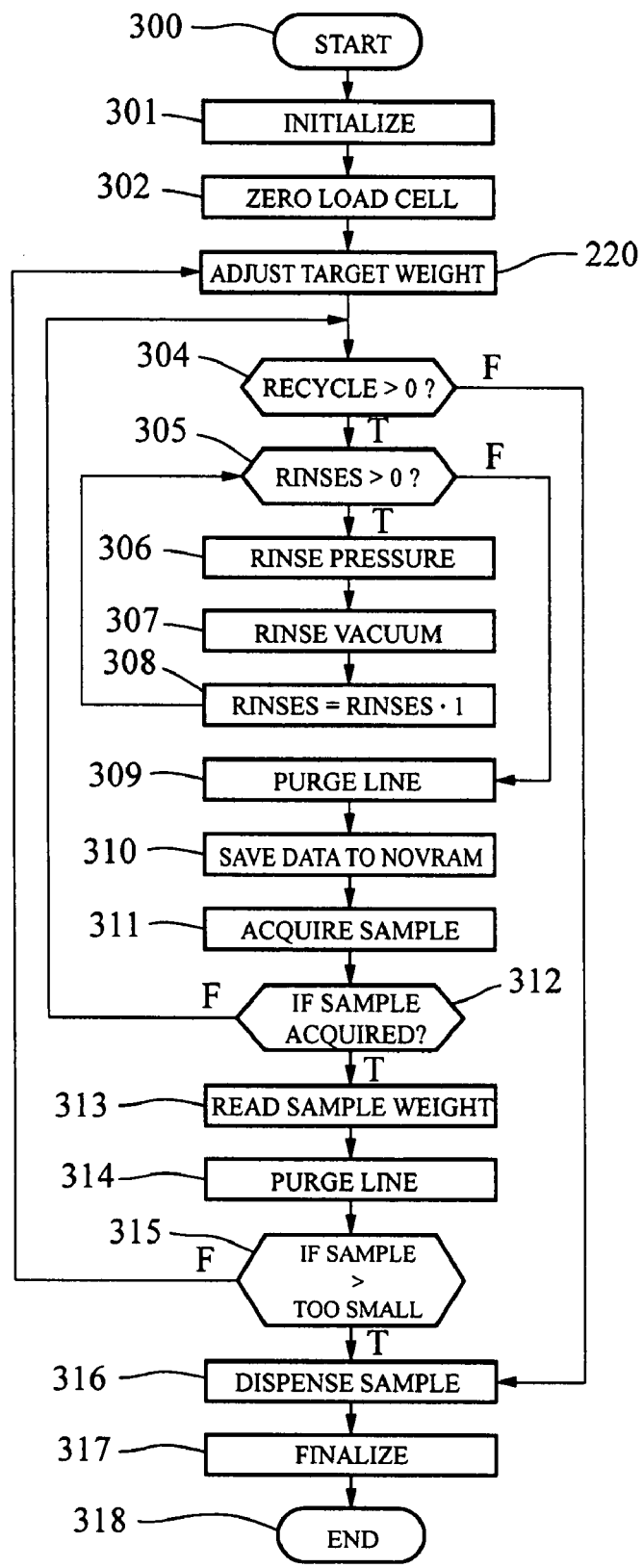

FIG. 12 illustrates the sampling process flow. The start condition 300 is determined under variable program control and is configured using the system menus. After the start 300 condition occurs, various system variables and logical outputs are initialized in step 301. This also sets the initial state of the air pump 8 (FIG. 1), the four-way valve 7, and the pinch valve 5. Next, a command is sent via the peripheral bus 19 to the load cell transducer 12 to zero the load cell measurement. Thus, any debris in the sampling chamber 2 or associated lines is compensated. Unless blocked by a prior exception condition, the algorithm 220 (FIG. 11) for adjusts the requested weight. The target weight is what the user inputs or selects. The above-described adaptive feedback process commences.

At this point the air pump is operational, the pinch valve is closed and the four-way valve is selected for pressure in the sampling chamber. The logical decision 304 (FIG. 12) involves a concept called recycle. Because the sample is measured after acquisition, there is a possibility with this invention to correct large errors in sample acquisition before accepting the sample. Recycle is the process of attempting multiple times to successfully acquire a sample. Typically at this point in the logic, the recycle value will be greater than 1. It could be greater than 1 depending on the user and/or factory configuration. The logical decision at 305 involves a concept called rinse. Rinse is the process of repeatedly alternately forcing material out of the sample tube and drawing material into the sample tube prior to sample acquisition. If the user and/or factory has configured for rinses then the processes 306, 307 and 308 will be repeated multiple times. This consists of pressurizing the sampling chamber forcing air down the sample port and out the sampling tube. This is maintained for a configurable time. The rinse vacuum process is accomplished by changing the state of the four-way valve 7, thus applying vacuum to the sampling chamber 2. This is maintained for a configurable time. The pressure 306 and vacuum 307 is alternately applied for a configurable number of times, in selectable RINSES step 308.

The next step (i.e., FIG. 12) is the PURGE LINE 309 process. The PURGE LINE 309 process timing is optionally configurable to accommodate varying installation configurations. PURGE LINE step 309 consists of pressurizing the sampling chamber 2 with the pinch valve 5 closed, forcing air out the sample port 3 and through the sampling tube. The objective is to remove retained material from the sampling tube prior to drawing fresh sample material. At this point, the sampling process is irreversibly committed. If the logic control 14 loses power during the subsequent processes, then the sample (indicated by liquid level 17 of FIG. 1) will fall by gravity into the sample storage system 13, but it will be unknown how much sample has been acquired. For this reason, the present state of the sampling process is saved to the non-volatile ram in step 310. If the logic controller, on power up, reads the non-volatile ram 95 and determines that a sampling cycle was started, but not finished normally, then exception logic is required to account for the indeterminate size sample.

The sample acquisition step 311 (FIG. 12) first sends a command over the peripheral bus 19 (FIG. 1) to the load cell transducer 12, instructing it to notify the logic controller 14 when it senses a mass equal to requested sample size 214. The pinch valve 5 remains closed. The four-way valve 7 is placed in the vacuum position pulling a vacuum on the sampling chamber 2. Sample is drawn from the source through the sample tube and into the sample chamber 2 via the sample intake port 3. During this time, the load cell transducer is continuously measuring the change in mass of the sampling assembly 1. When the requested sample size 214 is sensed, the load cell transducer 12 notifies the logic controller 14 that the sample is to be terminated. The logic controller terminates the sampling process by reversing the state of the four-way valve 7 forcing pressurized air into the sampling chamber 2 which after a short time stops the flow of sample and forces the sample material in the sample port 3 and the sampling tube back to the sample source. Various exception conditions can abnormally terminate this process; hence, the logical check step 312 determines if a sample is normally terminated. One such exception condition can be a clogging of the sample tube. Failure to acquire a sample redirects the process to just before the recycle check step 304.

A successfully acquired sample causes the logic controller 14 to after a stabilization time to request a final measurement of the sample weight read in step 313. The load cell transducer responds with a final reading which is recorded by the logic controller 14. The sample tube is purged again at step 314. The control conditions are identical to the purge line step 309. The duration time is user configurable. Prior to dispensing the sample, a final comparison is made at logical step 315. If the sample weight which was read in step 313 is below a pre-programmed lower limit, then control is passed back to the recycle step 304 via a calling of the adaptive feedback algorithm 220 (FIG. 11). Once a sample is successfully acquired or the recycle option terminates, then the sample is dispensed by step 316 into the sample storage system 13. There are many logical options related to sample dispensing depending on the type of sample storage system and the user programmed choices. These involve where to place the sample in the sequential sample storage system, when to terminate sampling, and overfill protection among others. Archival records are written with each sample and involve critical information about each sample, the time of day and date, and information about the sample storage system. Steps 317 and 318 complete the program.

The logical control 14 FIG. 1) can always be in either a program active state or in a user state. In the program active state, one of a multiplicity of preconfigured programs is active. These programs can be either factory default programs or individually configured by the user. The program can be in the running state or the idle state. In the idle state, a program is either awaiting a start signal or is idle after program termination. In the running state, a program can be waiting to begin the sample acquisition loop, between acquiring samples, or actively acquiring a sample. Various logical options can affect the state change between states. Active programs can be paused, temporarily blocking the acquisition of a sample without affecting the logic for determining when to acquire the next sample. Input from the user can terminate a program. Exception conditions can terminate a program. In the user state a multiplicity of user menus can be selected for performing various functions. These functions include factory configuration, factory test modes, program entry, archival management, and administrative functions including password management. Various portions of the user state are blocked from end-users and are reserved for factory related functions. Password protection of menus is layered allowing various levels of access.

What is claimed is:

1. A programmable liquid sampler for obtaining and digitally analyzing multiple, sequential samples in real time from an external source of liquid to be analyzed, said sampler comprising:

a sampling assembly for receiving and at least temporarily storing a sample, said assembly comprising a sampling chamber having an interior;

an intake sample port in fluid flow with said chamber interior for drawing liquid into said chamber in response to vacuum;

an air port in fluid flow communication with said chamber interior for either pressurizing said chamber or applying vacuum thereto;

pump means for generating either pressure or vacuum;

valve means for applying either pressure or vacuum from said pump means to said air port to either pressurize or apply vacuum to said chamber interior through said air port;

load cell means for determining the mass of a sample drawn into said sampling chamber interior in real time;

mechanical coupling means for securing the sampling assembly to said load cell means;

logic controller means for operating said sampler, said logic controller means interconnected with said load cell means for deriving data therefrom, said logic controller means comprising:

means for recognizing a desired target sample size inputted by a sampler operator;

means for requesting an initial sample by initiating sampling in response to said target sample size;

means for measuring the initial sample size;

means for developing a first scaling factor by comparing said target sample size to said measured sample size; and;

means for requesting and adjusting the size of a successive sample in response to said scaling factor.

2. The sampler as defined in claim 1 further comprising:

means for storing samples obtained with said sampler;

means for selectively discharging liquid from said sampling chamber into said means for storing, said discharging means comprising a discharge passage in fluid flow communication with said chamber interior, and valve means for controlling said discharge passage, said valve means in fluid flow communication with said means for storing samples.

3. The sampler as defined in claim 2 wherein said means for storing samples comprises a sequential storage system wherein successive samples are deposited into a plurality of different containers to segregate said samples in response to said logic controller.

4. The sampler as defined in claim 3 wherein said sequential sample storage system comprises a motor-driven rotary table controlled by said logic controller, indexing means for supplying table position information to said logic means, a container carrier disposed upon said table, and a plurality of radially spaced-apart sample containers held by said carrier.

5. The sampler as defined in claim 1 further comprising means for selectively varying the time delay between successive sampling cycles.

6. The sampler as defined in claim 1 further comprising means for selectively varying the quantity of liquid obtained in a given sample.

7. The sampler as defined in claim 1 further comprising means interconnected with said logic means for zeroing a reading from said load cell means.

8. The sampler as defined in claim 7 wherein said means interconnected with said logic means for zeroing a reading from said load cell means comprises:
   a first low pass filter for conditioning the output from said load cell means;
   differential amplifier means for instrumentation control, said differential amplifier means having first and second inputs and an output, the first differential amplifier means input receiving an output from said first low pass filter;
   a second low pass filter receiving the output from said differential amplifier;
   a second amplifier receiving the output of said second low pass filter;
   a third low pass filter receiving an output from said second amplifier;
   a third amplifier receiving and buffering an output from said third low pass filter that outputs to said logic controller;
   a variable voltage amplifier responsive to said logic controller, said variable voltage amplifier outputting to said second input of said differential amplifier.

9. A programmable liquid sampler for obtaining and digitally analyzing multiple, sequential samples in real time from an external source of liquid to be analyzed, said sampler comprising:
   a sampling assembly for receiving and at least temporarily storing a sample, said assembly comprising a sampling chamber having an interior;
   an intake sample port in fluid flow with said chamber interior for drawing liquid into said chamber in response to vacuum;
   an air port in fluid flow communication with said chamber interior for either pressurizing said chamber or applying vacuum thereto;
   pump means for generating either pressure or vacuum;
   valve means for applying either pressure or vacuum from said pump means to said air port to either pressurize or apply vacuum to said chamber interior through said air port;
   load cell means for determining the mass of a sample drawn into said sampling chamber interior in real time;
   mechanical coupling means for securing the sampling assembly to said load cell means;
   logic controller means for operating said sampler, said logic controller means interconnected with said load cell means for deriving data therefrom, said logic controller means comprising adaptive feedback means for correcting the obtained sizes of samples; and,
   means interconnected with said logic means for zeroing a reading from said load cell means.

10. The sampler as defined in claim 9 further comprising:
    means for storing samples obtained with said sampler;
    means for selectively discharging liquid from said sampling chamber into said means for storing, said discharging means comprising a discharge passage in fluid flow communication with said chamber interior, and valve means for controlling said discharge passage, said valve means in fluid flow communication with said means for storing samples.

11. The sampler as defined in claim 10 wherein said means for storing samples comprises a sequential storage system wherein successive samples are deposited into a plurality of different containers to segregate said samples in response to said logic controller.

12. The sampler as defined in claim 11 wherein said sequential sample storage system comprises a motor-driven rotary table controlled by said logic controller, indexing means for supplying table position information to said logic means, a container carrier disposed upon said table, and a plurality of radially spaced-apart sample containers held by said carrier.

13. The sampler as defined in claim 10 wherein said means interconnected with said logic means for zeroing a reading from said load cell means comprises:
    a first low pass filter for conditioning the output from said load cell means;
    differential amplifier means for instrumentation control, said differential amplifier means having first and second inputs and an output, the first differential amplifier means input receiving an output from said first low pass filter;
    a second low pass filter receiving the output from said differential amplifier;
    a second amplifier receiving the output of said second low pass filter;
    a third low pass filter receiving an output from said second amplifier;
    a third amplifier receiving and buffering an output from said third low pass filter that outputs to said logic controller;
    a variable voltage amplifier responsive to said logic controller, said variable voltage amplifier outputting to said second input of said differential amplifier.

14. The sampler as defined in claim 13 wherein said logic controller means comprising adaptive feedback means comprising:
    means for recognizing a desired target sample size inputted by a sampler operator;
    means for requesting an initial sample by initiating sampling in response to said target sample size;
    means for measuring the initial sample size;
    means for developing a first scaling factor by comparing said target sample size to said measured sample size; and;
    means for requesting and adjusting the size of a successive sample in response to said scaling factor.

15. A programmable method for obtaining multiple, sequential samples in real time from an external source of liquid to be analyzed, said method comprising the steps of:
   receiving and at least temporarily storing samples within a sampling chamber having an interior;
   intaking samples into said chamber in response to vacuum with a sample port in fluid flow with said chamber interior;
   applying either vacuum or pressure to said chamber interior in fluid flow communication with said chamber interior with a valve controlling the output of a pump;
   determining the mass of a sample drawn into said sampling chamber interior in real time with a load cell;
   deriving data from said load cell with a logic controller; and,
   correcting the size of samples through adaptive feedback steps comprising the sub-steps of:
   recognizing a desired target sample size inputted by a sampler operator;
   requesting an initial sample by initiating sampling in response to said target sample size;
   measuring the initial sample size;
   developing a first scaling factor by comparing said target sample size to said measured sample size; and;
   for requesting and adjusting the size of a successive sample in response to said scaling factor; and,
   storing samples obtained through said method by selectively discharging liquid from said sampling chamber.

16. The method as defined in claim 15 wherein including the steps of sequentially storing successive samples in a plurality of different containers to segregate said samples in response to said logic controller.

17. The method as defined in claim 15 including the step of automatically zeroing readings from said load cell.

18. The method as defined in claim 17 wherein said zeroing step comprises the sub-steps of:
   conditioning the output from said load cell with a first low pass filter;
   outputting the output of said first low pass filter into the first input of a differential amplifier having first and second inputs and an output,
   filtering the output from said differential amplifier with a second low pass filter;
   receiving and processing the output of said second low pass filter with a second amplifier;
   filtering the output from said second amplifier with a third low pass filter;
   receiving and buffering the output from said third low pass filter that outputs to said logic controller with a third amplifier;
   deriving a variable voltage responsive to said third amplifier and applying said variable voltage to said second input of said differential amplifier.

* * * * *